United States Patent [19]

Carmen, Raleigh A. et al.

[11] Patent Number: 5,104,788
[45] Date of Patent: * Apr. 14, 1992

[54] METHOD OF PREPARING NEOCYTES AND GEROCYTES IN A CLOSED SYSTEM

[75] Inventors: Carmen, Raleigh A., Concord; Randy B. Garcez, El Cerrito; Barry S. Leng, Pleasant Hill, all of Calif.

[73] Assignee: Miles Inc., Elkhart, Ind.

[*] Notice: The portion of the term of this patent subsequent to Jul. 24, 2007 has been disclaimed.

[21] Appl. No.: 364,756

[22] Filed: Jun. 12, 1989

[51] Int. Cl.$^5$ ............................................ A01N 1/00
[52] U.S. Cl. ................................. 435/2; 210/516; 210/782; 210/787; 210/749; 604/410; 436/63
[58] Field of Search ............... 210/516, 782, 787, 206, 210/749; 604/410; 435/2; 436/63

[56] References Cited

U.S. PATENT DOCUMENTS

| | | | |
|---|---|---|---|
| 4,596,657 | 6/1986 | Wisdom | 210/206 |
| 4,855,063 | 9/1989 | Carmen et al. | 210/749 |
| 4,892,537 | 1/1990 | Carmen et al. | 604/408 |
| 4,943,287 | 6/1990 | Carmen | 604/408 |
| 4,969,882 | 1/1990 | Carmen et al. | 604/410 |

Primary Examiner—David L. Lacey
Assistant Examiner—N. Edwards
Attorney, Agent, or Firm—James A. Giblin; Elizabeth F. Enayati

[57] ABSTRACT

A method of preparing neocytes and gerocytes in a closed blood bag system useful for the filtration of leukocytes from a red blood cell concentrate followed by the preparation and long term storage of neocytes and, preferably, gerocytes from the filtered concentrate. In very preferred embodiments, the system also provides containers for the expression of plasma and the preparation and long term storage of platelets.

5 Claims, 1 Drawing Sheet

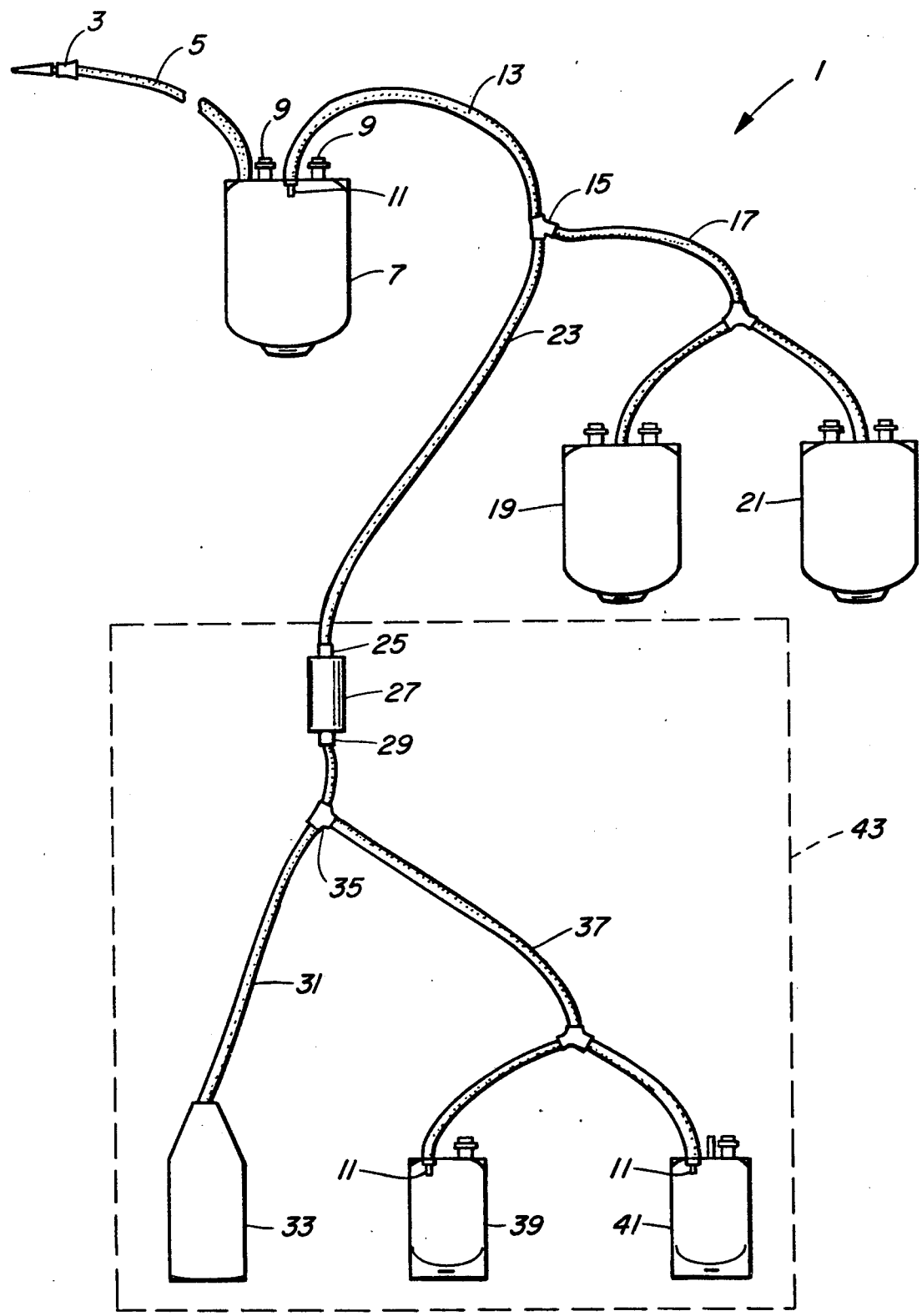

METHOD OF PREPARING NEOCYTES AND GEROCYTES IN A CLOSED SYSTEM

BACKGROUND OF THE INVENTION

1. Field

This disclosure is concerned generally with blood bags useful for the collection, processing and storage of blood and blood components. The disclosure is specifically concerned with a blood bag system useful for the preparation and long term storage of neocytes and gerocytes.

2. Prior Art

Plastic blood bag systems for the collection, processing and storage of blood and blood components are well known and have been used for thirty or more years. In early embodiments, when plastic films were used to make bags that ultimately replaced glass bottles, many of the plastic blood bag systems were "open" in the sense that there existed the chance of contamination as blood or separated blood components were moved into or out of the system. Quite often, the plastic bag system was a single bag having attached to it one or more tubings and ports for adding or removing bag contents. See, for example, U.S. Pat. No. 2,702,034 to Walter, U.S. Pat. No. 3,327,709 to Nehring et al., and U.S. Pat No. 3,416,528 to Kahn.

As the use of various components and sub-components of blood became accepted, attempts were made to avoid potential contamination problems by providing multiple blood bags attached to each other by tubings and including valving systems. See, for example, U.S. Pat. No. 3,058,799 to Rowles et al. and U.S. Pat. No. 4,332,122 to Williams. Such systems became known as doubles, triples, quads, etc., depending on the number of blood bags in the system. These multiple blood bag systems are known as "closed" in the sense that there no longer exists the chance of contamination after whole blood or a major component (e.g. plasma or a red cell concentrate) is introduced into and processed in the system.

Depending on design, the number of bags and such factors as valving systems and internal solutions, there now exists a variety of closed multiple blood bag systems. Available systems permit the collection, processing and storage of well known blood components such as red cell concentrates, plasma, and platelets.

In a typical application, whole blood is collected from a donor via a phlebotomy needle and passed through a plastic tubing into a first bag commonly known as the donor bag. The donor bag usually includes an anticoagulant solution to keep the whole blood from clotting. Connected to the donor bag via tubings and valves are one or more satellite bags in closed communication with the donor bag.

In one example, a triple multiple blood bag system consisting of a donor bag and two empty satellite bags is used to collect blood from a donor (into the donor bag). The entire triple system is then put in a centrifuge cup and centrifuged to form in the donor bag an upper lighter plasma portion and a lower heavier red blood cell (RBC) concentrate portion. After opening a valve in the system, the upper plasma portion is expressed into one of the satellite bags. This leaves the red cell concentrate behind in the donor bag which may be detached. The red cell concentrate is then commonly stored for up to 35 days before transfusion to a patient needing that type of RBCs.

The plasma-containing satellite bag may then be centrifuged to separate the plasma into an upper portion of platelet poor plasma and a lower heavier portion of platelet-concentrate. The upper platelet poor plasma may be expressed in to an empty satellite bag for subsequent pooling with other platelet poor plasma. Such plasma pools may then be fractionated into components such as albumin, coagulation factors, antibodies and the like. The remaining platelet concentrate may then be administered to a platelet deficient patient alone, or more commonly, after pooling with several other platelet concentrates.

Although blood bags have been available as singles, doubles, triples and quads, their use as closed systems has generally been limited to the basic type of separations and storage as described above for triples.

Recently, however, variations on the above basic system have been devised. For example, with the advent of so-called sterile docking systems (see U.S. Pat. No. 4,507,119 and U.S. Pat. No. 4,443,215), one can collect, process and store various blood components and still maintain a closed system with or without using the classic multiple blood bag systems. Sterile docking systems permit the communication of two originally disconnected bags but under conditions that do not jeopardize sterility during the communication process. Thus, sterile docked systems can be referred to as closed systems even though not originally connected as classic multiple blood bag systems.

Along with the above variations, including sterile docking, recent attention has been given to the use of blood bag designs for blood component enhancement. For example, an integral white blood cell (WBC) filter can be made part of a closed system for the preservation of red blood cells (RBC's). See U.S. Pat. No. 4,767,541 to L. Wisdom and U.S. Pat. No. 4,810,378 to R. Carmen et al. Further, as shown in EP Application No. 0,191,360 the geometry of blood bags may be specially modified to accomplish a finer separation of certain components such as neocytes and gerocytes. In addition, at least two closed systems have been described for the preparation of neocytes and gerocytes from a conventional red blood cell concentrate. In U.S. Pat. No. 4,416,778 to Rogers, a specially modified system of connected blood containers is shown for preparation of neocytes. In EPO Application No. 0,191,360, a double bag system is disclosed showing a specially designed bag (elongated and having a funnel shaped exit) for the separation of neocytes and their subsequent expression into a connected bag.

It is against the above background that the invention of the present disclosure arose. We have created a novel closed blood bag system which permits the filtration of RBC's and their subsequent processing into useable neocytes that, because of our system, can be stored for up to 42 days. Details of our system and methods of using it and its preferred variations are described below.

SUMMARY OF THE INVENTION

Our closed blood bag system for the preparation and long term storage of leukocyte-free neocytes comprises means for filtering leukocytes from a red blood cell concentrate being in direct closed communication with a bag for the separation of the concentrate into neocytes and gerocytes. The system also includes a bag containing a RBC preservative solution in closed direct communication with the separation bag. In use, a RBC mixture of neocytes and gerocytes is passed through the WBC filter means, removing at least about 98% of WBC's that are in the mixture. The filtered RBC's pass directly into the neocyte/gerocyte separation bag. This bag is then used to separate the heavier gerocytes from the lighter neocytes using centrifugal force. We have obtained a fine separation using the bag of EPO Application 0,191,360, the teachings of which are incorporated herein. That neocyte separation bag is elongated, and has a length to width ratio of at least 2:1, preferably at least 2.5:1.

Providing a RBC preservative solution in the communicating bag assures long term storage (up to 42 days) of the separated neocytes. After separation, the lighter neocytes are expressed into the bag originally containing the RBC preservative solution, leaving behind the gerocytes in a portion of the RBC solution. As far as we could determine, our system is the only one which provides for the closed long term storage of gerocytes as well as neocytes.

In preferred embodiments, the filter means is a WBC filter comprising a housing and an interior WBC filter material such as that described in U.S. Pat. No. 4,767,541 to L. Wisdom or U.S. Pat. No. 4,810,378 to R. Carmen et al. The filter has two ports, a first entrance port in sterile communication with another bag (e.g. a donor bag) containing or adapted to contain a RBC and WBC mixture. In sterile communication with the donor bag are at least two other bags for collecting plasma and platelets. The platelet bag may be a long term (e.g. at least 5 days) platelet storage bag made from a film which permits gas transmissivity useful for platelet storage. This film may be a polyolefin material having the desired gas transmissivity (e.g. U.S. Pat. No. 4,140,162 to Gajewski et al.) or, preferably, TOTM plasticized PVC film of U.S. Pat. No. 4,280,497 to R. Carmen et al.

Details of our system and preferred variations are described in more detail below.

BRIEF DESCRIPTION OF THE FIGURES

The figure shows a plan view of a very preferred embodiment of this disclosure, a key feature of which is enclosed within the dotted-line box 43.

SPECIFIC EMBODIMENTS

Our preferred system to date is shown in the Figure. As can be seen in the Figure, the preferred system comprises a total of six bags of various types in closed communication with an intermediately located filter means.

The preferred system can be described in terms of its use and the various processing and storage steps which permit the preparation and long term storage of neocytes and, preferably, gerocytes.

Whole blood is drawn from a donor using a conventional phlebotomy needle 3. The blood is collected via conventional PVC tubing 5 into a conventional donor bag 7 which contains an anticoagulant such as citrate-phosphate-double dextrose. Bag 7 may be made of conventional blood bag film such as DEHP plasticized PVC (e.g., see U.S. Pat. No. 4,222,379 to Smith) and has a volume large enough to accommodate both the anticoagulant and a unit of donated whole blood (e.g. total volume for bag 5 is about 600 ml). Bag 7 typically includes one or more conventional blood bag port structures 9 and an internal frangible valve 11 such as that described in U.S. Pat. No. 4,586,928 to Barnes et al. Such a frangible valve 11 is preferred and can also be seen in bags 39 and 41, described below.

After the plasma and RBC's are separated by centrifugation of bag 7, valve 11 is opened by external manipulation and the upper plasma is expressed via tubing 13 through the right side of Y device 15 through tubing 17 into bag 19. The plasma may include blood platelets. Tubing 17 may now be cut and sealed using conventional techniques leaving bag 19 containing the plasma and platelets still in closed communication with bag 21. The contents of bag 19 are centrifuged and the lighter platelet poor plasma is expressed into bag 21. Bags 19 and 21, unlike donor bag 7, are preferably made from a plastic film having a high gas transmissivity (see, for example, U.S. Pat. No. 4,280,497 to R. Carmen et al., incorporated herein).

After the plasma has been expressed from donor bag 7 to bag 19, a RBC concentrate remains in donor bag 7. After reconstitution, with a RBC preservative solution, already in the closed system such as the solution in bag 41 (which is also used to prime the filter 27), the RBC mixture (unseparated neocytes, gerocytes and leukocytes) is passed via tubing 13 through the left side of Y device 15 and tubing 23 into the first port 25 of filter 27 which is adapted to remove at least about 98% of WBCs from the mixture and can be like that of U.S. Pat. No. 4,767,541 to L. Wisdom or U.S. Pat. No. 4,810,378 to R. Carmen et al.

Filtration is preferably by gravity. The RBC's then pass from filter 27 through second port 29 past Y device 35 via tubing 31 into neocyte/gerocyte separation bag 33, very preferably of the elongated conventional funnel-ended type described in EPO Application No. 0,191,360. A conventional seal is made on the tubing between filter exit port 29 and Y device 35 and bags 33, 39 and 41 are detached. The bags are centrifuged as described in EPO Application 0,191,360 to form a cell-free upper layer (preservative solution plus residual plasma) and a lower layer of density-separated red cells (both neocytes and denser gerocytes). Approximately ½ volume of upper layer (preservative solution plus residual plasma) is expressed into bag 41. The remaining upper layer (preservative solution plus residual plasma) and about the upper ½ of the red cells (the less dense neocytes) are expressed into final neocyte storage bag 39 (about 200 mL volume). Preservative solution plus residual plasma in bag 41 is added back to bag 33 to reconstitute the remaining red cells (gerocytes). The reconstituted gerocytes are transferred bag to bag 41 for long term storage. The neocytes in bag 39 are capable of storage for up to 42 days, depending upon the storage solution used. An example of such a 42 day RBC storage or preservative solution is AS-3, described by Simon et al. (Transfusion 1987, 27:178–182).

An added bonus of this disclosed system is that the gerocytes (presently often simply discarded) are maintained in the closed system and also in a preservative solution. Uniquely, this is all accomplished within a closed blood bag system. Thus, the gerocytes are not wasted and can be used in cases where RBC age is not a concern (e.g. where RBC's of a given type are given in relatively small, non-recurring amounts and where iron overload is not a concern).

A very unique aspect of our closed system is within the dotted box 43 and we are unaware of any disclosure or even a suggestion that both neocytes and gerocytes can be prepared for long term storage in a system that includes an integral filter for removing WBC's, the inclusion of which can limit duration of RBC storage. We are also unaware of any such system which provides the RBC storage solution in a closed system with both the filter and the neocyte/gerocyte separation bag.

In an actual neocyte separation and storage method using our preferred system described in the Figure, we were able to prepare neocytes from packed RBC's from which at least 98% of all WBC's were filtered out. In combination with the RBC storage solution (e.g. AS-3), these neocytes could be stored successfully for up to 42 days and still be used in a patient. These results are obtained because of the novel closed system of this disclosure.

Although a key feature of this disclosure is the sub-system within the dotted line box of the figure, our preferred system includes all components of the figure, including pre-attached donor bag 7 and satellite bags 19 and 21. It can be appreciated, however, that a bag containing RBC's can be sterile docked into the sub-system within dotted line box 43 at, for example, a point on tubing 23 while still maintaining a closed system.

Unless otherwise indicated above, conventional blood handling techniques and materials can be used in making and using our novel system. All terms used (e.g. sterile, sterile connection, etc.) have their conventional meaning known to those skilled in the art. As used herein, RBC storage solution, RBC preservative solution and RBC additive solution are used interchangeably and should be considered equivalent.

Given the above disclosures, it is thought that numerous variations will occur to those skilled in the art. Accordingly, it is intended that the above described preferred system should be considered as illustrative and that the scope of the invention disclosed should be limited only by the following claims.

We claim:

1. A method of preparing neocytes and gerocytes in a closed system comprising the steps of
   (a) introducing a suspension of packed red blood cells and white blood cells into a filter having an entrance port and an exit port and capable of removing substantially all white blood cells from the suspension;
   (b) collecting the filtered red blood cells into a separation bag constructed so as to separate red blood cells into neocytes and gerocytes;
   (c) separating the cells of step (b) into neocytes and gerocytes;
   (d) expressing the neocytes into a first bag in direct sterile communication with the separation bag and containing a solution selected from a saline solution and a red blood cell storage solution;
   (e) reconstituting the gerocytes of step (c) with a solution from a second bag in direct sterile communication with the separation bag; and
   (f) expressing the reconstituted gerocytes into the second bag, steps (a) through (f) all being accomplished within a closed blood bag system.

2. The method of claim 1 wherein prior to step (c), the hematocrit of the non-separated red blood cells is determined and that determination is used to determine the amount of neocytes to be expressed in step (d).

3. The method of claim 1 wherein prior to introducing the suspension into the filter, an aqueous solution is passed through the filter.

4. The method of claim 3 wherein the aqueous solution is a saline solution or a red blood cell storage solution.

5. The method of claim 3 wherein the aqueous solution is contained in a bag in direct sterile communication with the filter and the separation bag and the aqueous solution is passed through the filter by introducing it into the exit port of the filter.

* * * * *